(12) United States Patent
Hughes et al.

(10) Patent No.: US 7,488,406 B2
(45) Date of Patent: Feb. 10, 2009

(54) APPARATUS FOR COLLECTING PARTICLES

(75) Inventors: Michael Pycraft Hughes, Guildford (GB); Kai Friedrich Hoettges, Guildford (GB)

(73) Assignee: The Secretary of State for Defence (GB)

( * ) Notice: Subject to any disclaimer, the term of this patent is extended or adjusted under 35 U.S.C. 154(b) by 391 days.

(21) Appl. No.: 10/545,116

(22) PCT Filed: Feb. 12, 2004

(86) PCT No.: PCT/GB2004/000533

§ 371 (c)(1),
(2), (4) Date: Aug. 10, 2005

(87) PCT Pub. No.: WO2004/071668

PCT Pub. Date: Aug. 26, 2004

(65) Prior Publication Data

US 2006/0070957 A1    Apr. 6, 2006

(30) Foreign Application Priority Data

Feb. 12, 2003   (GB)   .................... 0303305.7

(51) Int. Cl.
G01N 27/447 (2006.01)
G01N 27/453 (2006.01)
(52) U.S. Cl. .................. 204/547; 204/643; 204/600; 204/450
(58) Field of Classification Search ............... 204/547, 204/643, 600, 450
See application file for complete search history.

(56) References Cited

U.S. PATENT DOCUMENTS

| 4,571,292 | A | 2/1986 | Liu et al. |
| 5,512,159 | A | 4/1996 | Yoshioka et al. |
| 5,589,047 | A | 12/1996 | Coster et al. |
| 6,264,825 | B1 * | 7/2001 | Blackburn et al. ....... 205/777.5 |

(Continued)

FOREIGN PATENT DOCUMENTS

EP   1145766   10/2001

(Continued)

OTHER PUBLICATIONS

Wong et al. "An AC Electroosmotic processor for Biomolecules," Transducers '03, International Conference on Solid-State Sensors, Actuators and Microsystems, Digest of Technical Papers, 12th, Boston, MA, United States, Jun. 8-12, 2003, vol. 1, 20-23 Publisher: Institute of Electrical and Electronics Engineers, New York, N.Y.*

(Continued)

*Primary Examiner*—Alex Noguerola
(74) *Attorney, Agent, or Firm*—Dean W. Russell; Kilpatrick Stockton LLP (57) ABSTRACT

Detail is apparatus for collecting particles from a liquid, including a first electrode having an upper surface defining one or more substantially circular areas of a predetermined diameter separated from a counter electrode, having an uppersurface bounding at least in part the circular area or areas of the first electrode, by a predetermined gap and equipment for applying an alternating potential difference of a predetermined magnitude at a predetermined frequency lower than the charge relaxation frequency of the liquid across the electrodes whereby particles from the liquid are focused onto the circular area or areas of the first elect through an induced electro-osmotic flow in the liquid.

16 Claims, 8 Drawing Sheets

U.S. PATENT DOCUMENTS

2002/0031838 A1     3/2002     Meinhart et al.
2002/0036139 A1     3/2002     Becker et al.
2003/0048452 A1     3/2003     Johansen

FOREIGN PATENT DOCUMENTS

GB             2197068 A    *    5/1988
WO       WO 01/42768          6/2001
WO       WO 2004/074819      9/2004

OTHER PUBLICATIONS

Ramos et al. Ac electrokinetics: a review of forces in microelectrode structures, J. Phys. D: Appl. Phys. 31 (1998) 2338-2353.*

Green et al. "Fluid Flow induced by nonuniform ac electric fields in electrolytes on microelectrodes. I. Experimental measurements" Physical Review E, vol. 61, No. 4, Apr. 2000, 4011-4018.*

González et al. "Fluid Flow induced by nonuniform ac electric fields in electrolytes on microelectrodes. II. A linear double-layer analysis" Physical Review E, vol. 61, No. 4, Apr. 2000, 4019-4028.*

A. Ramos, et al., "AC Electric-Field-Induced Fluid Flow in Microelectrodes," *J. Colloid and Interface Science*, vol. 217, pp. 420-422 (1999).

Y. Liu, et al., "Immersed electrokinetic finite element method," *Int. J. Numer. Meth. Engng 2007*, vol. 71, pp. 379-405 (2006).

* cited by examiner

APPARATUS FOR COLLECTING PARTICLES

CROSS REFERENCE TO RELATED APPLICATIONS

This application is the U.S. national phase of International Application No. PCT/GB2004/000533 filed on February 12, 2004 and published in English on August 26, 2004 as International Publication No. WO 2004/07 1668 A1 which application claims priority to Great Britain Application No. 0303305.7 filed on February 12, 2003, the contents of which are incorporated by reference herein.

FIELD OF THE INVENTION

The present invention is generally concerned with apparatus for collecting particles. The present invention is particularly, although not exclusively, directed to surface bound sensors incorporating planar electrode configurations capable of collecting or focusing particles from a liquid on an upper surface thereof.

BACKGROUND OF THE INVENTION

The optical detection of particles, such as bacteria and viruses, adhered to a sensing medium by monitoring changes in refractive index of the medium and/or light scattered or emitted from the particles is a well-known technique. See, for example, International Patent application WO 01/42768 and references therein.

However, the sensitivity of the technique is limited by slow diffusion of the particles in the liquid to the sensor surface, even with stirring or agitation. Consequently, there is a need to improve the concentration of particles on the sensing medium of sensor surfaces.

It is well-known that a particle can become polarised in an inhomogeneous electric field and that the interaction of the induced dipole with the field leads to the movement of the particle towards or away from the area of field inhomogeneity. These effects, termed positive or negative dielectrophoresis respectively, depend on the properties of the particle and the liquid. Dielectrophoresis forms the basis for the separation of particles in a large number of apparatus.

However, one problem with the application of the technique so as to enhance particle deposition to a sensing surface, is that the areas of greatest electric field inhomogeneity are at the electrode edges. Consequently, particles accumulate at the edges and not on the surface of the planar electrodes.

A third form of dielectrophoresis can be used to separate submicrometre particles between planar electrodes (N. G. Green and H. Morgan, J. Phys. D, Appl. Phys., 1998, 31, L25-L30). The technique, known as "abnormal dielectrophoresis" because particles can collect on the surface of the electrodes, relies on an induced electro-osmotic flow in the bulk liquid when an alternating potential difference is applied to the electrodes. The bulk flow, which is driven by an interaction between the oscillating electric field and the diffuse double layer of charge on the electrodes, originates in the gap between the electrodes, and progresses over the surface of each electrode. For a detailed explanation, see N. G. Green et al., J. Colloid Interface Science, 1999, 217, 420-422 and N. G. Green et al., J. Am. Phys. Soc., 2000, Physical Review E, 61, 4011-4018 and 4019-4028.

At a certain threshold flow velocity, at which positive dielectrophoretic forces are overcome by drag forces, the bulk flow moves the particles onto the electrode surfaces. The particles collect along the surface of the electrodes at the point where the bulk flow diminishes or converges with a bulk flow originating from an opposing edge of the same electrode. The particles are apparently held on the surface of the electrode by one or more of a positive dielectrophoretic force, flow stagnation and gravity.

The present invention starts from the realisation that the application of an electric field at or adjacent a sensor surface may offer increased sensitivity for the detection and/or assay of particles. In particular, abnormal dielectrophoresis may be particularly suitable in that particles are collected on an upper surface of an electrode.

The present invention generally aims to provide an improved electrode configuration capable of focusing particles on an electrode surface thereof. The present invention, also aims to provide surface bound sensors associated with or incorporating an electrode configuration which is capable of collecting or focusing particles from a liquid onto an electrode surface.

Accordingly, in one aspect, the present invention provides apparatus for collecting particles, comprising a first planar electrode having an upper surface defining one or more substantially circular areas separated from a planar counter electrode having an upper surface bounding, at least in part, the circular area or areas of the first electrode by a predetermined gap and means for applying an alternating potential difference of a predetermined magnitude, at a predetermined frequency lower than the charge relaxation frequency of the liquid, across the electrodes whereby particles from a liquid are focused onto the circular area or areas of the first electrode through an induced electro-osmotic flow in the liquid.

It will be understood that the term "substantially circular" does not strictly require that the area or areas, which it qualifies, are wholly or truly circular. In particular, it will be apparent that the contribution of the present invention is to provide for the collection of particles by convergence of bulk flows in the liquid originating at or adjacent the bounded edges of an electrode. Thus, the term "substantially circular" may refer to whole or partially interrupted circles as well as to distorted circles.

In preferred embodiments of the present invention, the counter electrode comprises a surface bounding at least the most part of the circular area or areas of the first electrode.

In some embodiments, the upper surface of the first electrode is wholly circular and the upper surface of the counter electrode provides a wholly unbroken circular recess there around. In this embodiment the counter electrode can comprise a ring electrode surrounding the first electrode. However, these embodiments are difficult to fabricate in that the first electrode can only be connected to an alternating signal source by covering a portion of the counter electrode with an insulating material.

In another embodiment, therefore, the upper surface of the first electrode defines a circular area having a leg portion and the counter electrode comprises a broken ring surrounding the major part of the circular area of the first electrode. In this "lollipop" embodiment, the interruption in the ring bounds a portion of the leg portion of the first electrode surface.

Preferably, however, the electrode configuration is interdigital. In some embodiments, the upper surface of the first electrode comprises a plurality of circular areas having a common, horizontal central axis connected by connecting arm portions. The arms may lie on or alternatively be offset from the common axis of the circular areas. In these "pearl chain" embodiments, the counter electrode may comprise a plurality of recesses and "leg" or "tooth" portions bounding neighboring circular areas of the upper surface of the first electrode. Preferably, the leg or teeth portions define opposing, arcuate edges so as to increase the circular areas bound by the counter electrode.

In a particularly preferred embodiment of the present invention, the upper surface of the first electrode defines a plurality of circular areas, sharing a common horizontal central axis, each having a connecting limb, substantially perpendicular, to the main body or "bus bar" of the electrode. In this embodiment, the common axes of the first electrode and the counter electrode are arranged parallel to one another with the limbs and bus bar of each electrode bounding the most part of each circular area of the other electrode.

It will be understood that the latter configuration is particularly advantageous in that particles are also focused on the circular areas of both the first electrode and the counter electrode. The configuration therefore provides optimal use of the electrode surfaces for focussing particles and is easily fabricated in a single step.

The circular area or areas of the electrode configurations of the present invention, may comprise a wide range of diameters. In particular, the diameter of the, or each circular area may be between one and three orders of magnitude higher, than the size of the particles of interest. By contrast, conventional electrode configurations supporting abnormal dielectrophoresis (see for example N. G. Green and H. Morgan, J. Phys., D, Appl. Phys., 1998, 31, L25-L30) employ surfaces having diameters which are limited to a single order of magnitude greater than particle size. The present invention is not restricted by this apparent requirement, which is thought necessary to maintain an appropriate electric field gradient. Without wishing to be bound by theory, the collection or focusing of particles would appear to depend largely on the generation of the bulk flow in the liquid.

The bulk flow induced in the liquid comprises vortices developing at the edges of the circular areas and extending over their surfaces. The size of each vortex is independent of the size of the electrode but dependant, for a given conductivity of the liquid, on the magnitude and frequency of the applied alternating potential difference applied to the electrodes. The size of each vortex peaks at a certain frequency of the applied potential difference.

The bulk flow in the liquid is also influenced by the extent of the gap between the first electrode and the counter electrode. In particular, the electro-osmotic flow, which is dependent on the on the strength of the electric field, is inversely proportional to the extent of the gap between the electrodes.

The diameter of the electrode surfaces and the extent of the gap between them are chosen so as to enable large vortex sizes to operate in the liquid without overlap on the electrode surfaces. Preferably, the diameter of the electrode surfaces is relatively large compared to the prior art. Still more preferably, the diameter of each circular area ranges from 200 to 1000 μm. Preferably, the extent of the gap ranges from 10 to 200 μm. Still more preferably, the extent of the gap ranges from 75 to 100 μm.

The choice of frequency and magnitude of the applied potential difference for a particular electrode configuration, particle size and liquid conductivity is a matter of routine experimentation. The frequency and magnitude of the applied potential difference are chosen so that the vortices developed in liquid do not overlap on the electrode surfaces. Preferably, the frequency, which may be higher or lower than the frequency at which the size of the vortices is greatest, is chosen so that the diameter of the vortices are just below the radius of the circular area and particles are focused to a tight spot. However, frequencies in which the diameter of the vortices is smaller and particles are collected in a ring may be used.

It will be appreciated that the electrode configuration of the present invention enables relatively large vortices to "reach out" into the liquid to "pull down" the particles to the electrode surfaces. The present invention offers improved sensitivity in detection of the particles not just through focusing of particles but also through the concentration effect of relatively large vortices.

The electrodes of the present invention may comprise any suitably conducting material. Preferably, the thickness of the conducting material ranges from 10 nm to 50 μm. The electrodes may be disposed on any convenient substrate comprising an insulating material. Preferably, the substrate comprises a glass or an optically transparent material. The apparatus of the present invention may, therefore, comprise a chip, which can be conveniently fabricated by photolithography and wet etching a layer of indium tin oxide (ITO) or gold on a glass substrate.

The apparatus of the present invention may comprise an array of one or more electrode configurations, comprising any number of circular areas, capable of collecting or focusing particles on a surface of an electrode.

The present invention allows focusing of particles having a wide range of diameters on a single electrode configuration or array. For example, electrode configurations defining surfaces having circular diameters ranging from 200 to 1000 μm, and a gap ranging from 10 to 200 μm are capable of tightly focusing cells, bacteria and viruses from an aqueous sample.

In particular, particles of diameter ranging from 20 nm to 5 μm suspended in aqueous liquids ranging in conductivity from 10 to 90 mS/m may be focused by applying a potential difference ranging in frequency from 0.6 to 2.5 kHz and voltage from 1 to 20 V. However, frequencies ranging from 200 to 10,000 Hz may be used depending on the conductivity of the liquid.

It will be understood from the above, that the apparatus of the present invention may comprise a surface plasmon resonance (SPR) chip enabling particles to be detected by a change in the SPR angle of light incident the chip and/or by scattering or emission of light from the particles.

In a preferred embodiment, the chip includes a sensing medium capable of retaining the collected or focused particles. The sensing medium may comprise a coating or layer of one or more molecules capable of selectively binding particles of interest—such as antibodies or lectin molecules.

In these embodiments, the apparatus may comprise a metal-clad (or dye-clad) leaky waveguide (MCLW) sensor such as those described in our co-pending international patent application PCT/GB2002/04545.

Further, the antibody layer, for example, may be provided over one or more circular areas of the electrode. Of course, different antibody layers may be provided over different circular areas of the electrode or, where more than one electrode pair is used, over different electrodes.

In a second aspect, the present invention provides a method for collecting particles from a liquid, comprising the steps of i) introducing the liquid to apparatus comprising a first electrode, having an upper surface defining one or more substantially circular areas of predetermined diameter, separated from a counter electrode, having an upper surface bounding at least in part the circular area or areas of the first electrode, by a predetermined gap and ii) applying an alternating potential difference of a predetermined magnitude at a predetermined frequency lower than the charge relaxation frequency of the liquid whereby to induce an electro-osmotic flow in the liquid that focuses the particles onto the circular area or areas of the first electrode.

In one embodiment of the method, the magnitude and frequency of the predetermined alternating potential is chosen, for a particular electrode configuration, particle size and liquid conductivity, so that the electro-osmotic flow defines vortices of size just below the radius of the circular area or areas of the first electrode. In this embodiment the focusing of the particles is tightly confined to the centre of each focusing surface.

As mentioned above, preferably the magnitude and frequency of the predetermined alternating potential is also chosen, for a particular electrode configuration and liquid conductivity, so that the vortices "reach out" into the bulk of the liquid to "pull down" the maximum possible number of particles.

For liquids of conductivity ranging from 10 to 90 mS/m, the applied potential difference preferably ranges in frequency from 0.6 to 2.5 kHz and voltage from 1 to 20 V when the diameter of the circular area or areas ranges from 200 to 1000 µm and the gap between electrodes ranges from 10 to 200 µm. However, as mentioned above, frequencies ranging from 200 to 10,000 Hz may be used depending on the conductivity of the liquid.

In one embodiment of the method, the frequency and magnitude of the applied potential difference is chosen, for a particular electrode configuration and liquid conductivity, so that viruses are tightly focused. In another embodiment, the magnitude and frequency of the applied potential difference is chosen, for a particular electrode configuration and liquid conductivity, so that bacteria are tightly focused. It will be apparent therefore that the present invention enables the focused collection of a wide range of particles. In particular, it is expected that particles ranging in diameter from 20 nm to 5 µm may be focused.

Where the apparatus of the present invention comprises an SPR or MCLW chip, the method of the present invention enables the detection and/or assay of particles in the liquid. As mentioned above, the particles may be detected by a change in the SPR angle of light incident the chip and/or by scattering or emission of light from the particles.

In a preferred embodiment, the method uses a chip incorporating a sensing medium, such as an antibody or lectin coating or layer, capable of retaining the collected or focussed particles. In this embodiment, the particles may be retained when the electrode power or signal source is turned off.

The method of the present invention may be adapted to remove (or "wash") particles from an electrode surface on which they are collected or bound, for example, by antibody coating or layer. In particular, the frequency of the signal source is chosen so that the vortices in the fluid overlap the electrode surface.

In one embodiment, particles not retained over the electrode surface by bonding with, for example, an antibody or lectin, are washed away by the fluid. The particles of interest may be separated from, for example, unwanted particles such as dust.

The association of a surface bound sensor with an electrode configuration providing an electric field offers the advantage of increased sensitivity in the detection and assay of particles in a liquid. In particular, apparatus including an electrode or electrodes supporting abnormal dielectrophoresis are less sensitive to the particular properties of the particles in that they principally rely on bulk flow in the liquid rather than their interaction with an electric field. Thus, a single apparatus may be used for the collection and detection of a wide range of particles including viruses, bacteria and cells.

The incorporation of the electrode or electrodes into the surface of the sensor enables easy fabrication and the relatively low frequencies used can be generated by standard signal generators and amplifier chips offering low power consumption.

BRIEF DESCRIPTION OF THE DRAWINGS

The present invention will now be described by reference to a number of examples and the following drawings in which FIGS. 1 a) and b) are schematic illustrations highlighting the collection of particles from a liquid onto an electrode surface through abnormal dielectrophoresis;

FIGS. 2 a) to c) are plan views of a number of different embodiments of the electrode configuration according to the present invention;

FIGS. 4 a) to c) are photographs highlighting the collection of *bacillus subtilis* var. *Niger* (*bacillus globigii*) spores on the electrode surfaces of the embodiment of FIG. 3;

FIGS. 5 a) and b) are graphs showing respectively the collection of particles on the electrode surfaces of the embodiment of FIG. 3 as a function of time and as a function of the frequency of the alternating applied potential difference;

FIGS. 9 a) and b) are schematic illustrations showing respectively a SPR chip according to the present invention and its use with a suitable flow cell.

Figure 1A:
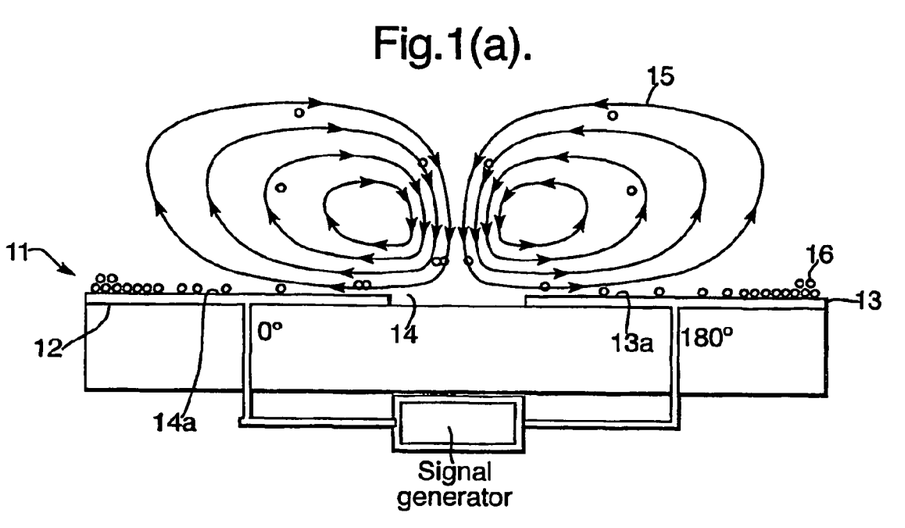

Having regard now to FIG. 1 a), there is shown a known electrode configuration, generally designated 11, having first and second planar electrodes 12, 13 defining a gap 14 between them. An alternating potential difference applied across the electrodes 12, 13 at low frequency (<100 kHz) leads to an inhomogeneous electric field that exerts "electro-osmotic" forces on a liquid in contact with the electrodes.

The forces acting on the liquid generate a bulk flow or vortices 15 in the liquid which, provided the frequency of the applied potential difference is lower than the charge relaxation frequency of the liquid, originates in the gap 14 and moves out across each electrode surface 12a, 13a.

The bulk flow 15 creates drag forces, which act on particles 16 suspended in the liquid. At a critical point, depending on the magnitude and frequency of the applied potential difference, their magnitude is sufficient to overcome dielectrophoretic forces so that particles 16 entrained in the bulk flow in the gap are moved from the edges out across the surface 12a 13a of the electrodes. However, because the electric field is more uniform over the electrode surfaces 12a 13a and the bulk flow 15 diminishes, the upward drag acting on the particles is now insufficient to overcome the dielectrophoretic forces and/or gravity.

Figure 1B:
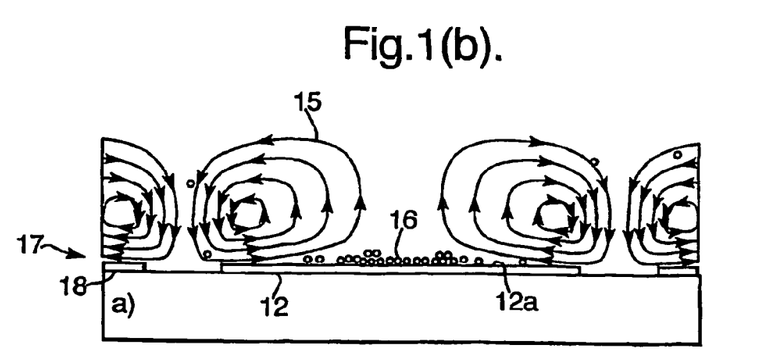

FIG. 1 b) shows part of a known electrode configuration, generally designated 17, in which a surface 12a of a first planar electrode 12 is bounded at opposing edges by surfaces of an adjacent counter electrode 18. As may be seen, abnormal dielectrophoresis leads to vortices 15 covering substantially the whole of the surface 12a of the first electrode 12 so that the leakage of particles 16 away from the surface is effectively contained. The particles 16 are collected on the electrode surface 12a in a line parallel to the longitudinal length of the electrode 12.

Figure 2A:
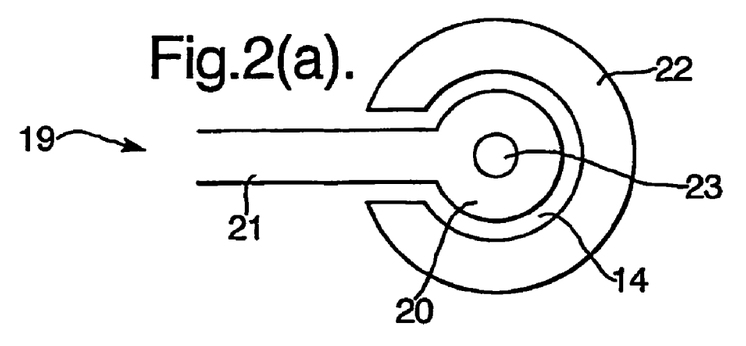

Referring now to FIG. 2 a), there is shown a first, practical embodiment of an electrode configuration according to the present invention. The electrode configuration, generally designated 19, comprises a first, substantially circular, planar electrode 20 having a leg 21 separated from a counter electrode. The counter electrode comprises an interrupted ring electrode 22, which substantially bounds the first electrode 20 and a portion of the leg 21. Because the first electrode 20 is near circular and bounded around most of its circumference particles 16 collect thereon in a ring, which can be tightly focused to a spot 23 by selection of appropriate parameters. The focusing of particles 16 is due to a plurality of inwardly extending vortices 15 forming around the cirumferential edge of the electrode 20.

Figure 2B:
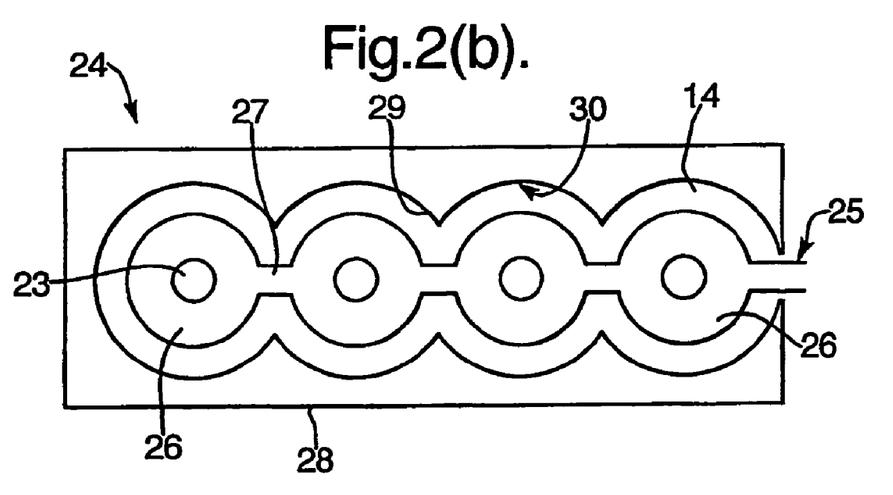

FIG. 2 b) shows an interdigital electrode configuration generally designated 24. A first planar electrode 25 comprises four near circular surfaces 26 linked along a central horizontal axis by arm portions 27. A planar, counter electrode 28 defines a surface 28a having a pair of toothed leg portions 29 and recesses 30 that complement the circular surfaces 26 and encompass the first electrode 25. Particles 16 are focused in a ring or spot 23 on each of the circular surfaces 26 of the first electrode 25.

Figure 2C:
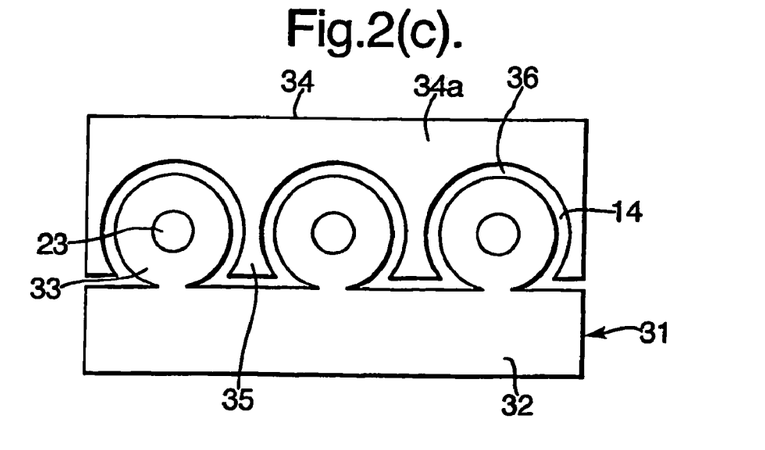

FIG. 2 c) shows a further interdigital electrode configuration. A first planar electrode 31 comprises a linear strip or "bus bar" 32 having three protruding near circular surfaces 33, which share a common central horizontal axis. A planar counter electrode 34 defines a surface 34a having four leg portions 35 and recesses 36 that complement the circular surfaces and encompass the first electrode 31. Particles 16 are focused in a ring or spot 23 on each of the circular surfaces 33 of the first electrode 31.

Figure 3:
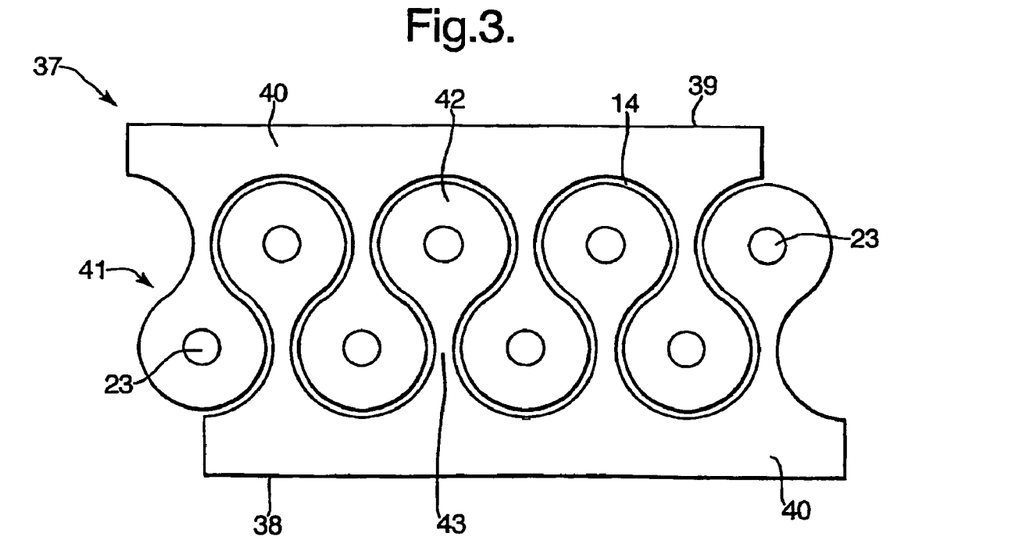
FIG. 3 is a plan view of a preferred embodiment of the electrode configuration according to the present invention.

FIG. 3 shows another interdigital electrode configuration, generally designated 37, which makes optimal use of the electrode surfaces for collecting or focusing particles 16. Each electrode 38 39 comprises a strip or bus bar 40 having four thumb sections 41 extending perpendicular to its longitudinal length. Each thumb section 41 defines a near circular surface 42 linked to the strip by an arm 43, and together with the bus bar 40 provides complementary recesses 44 for the thumb sections 41 of the other electrode. Particles 16 are focused in a ring or spot 23 on the circular surfaces 42 of each electrode 38, 39.

EXAMPLE 1

The electrode configuration 37 of FIG. 3, in which the circular surfaces 42 of each electrode 38, 39 are 575 µm and the gap size is 100 µm, is used to focus spores 16 of *bacillus globiggi* (~800 nm) from a 30 mS/m potassium chloride solution containing ~10$^8$ spores/ml at an applied alternating potential difference of 1 kHz frequency at 10V.

Figure 4A:
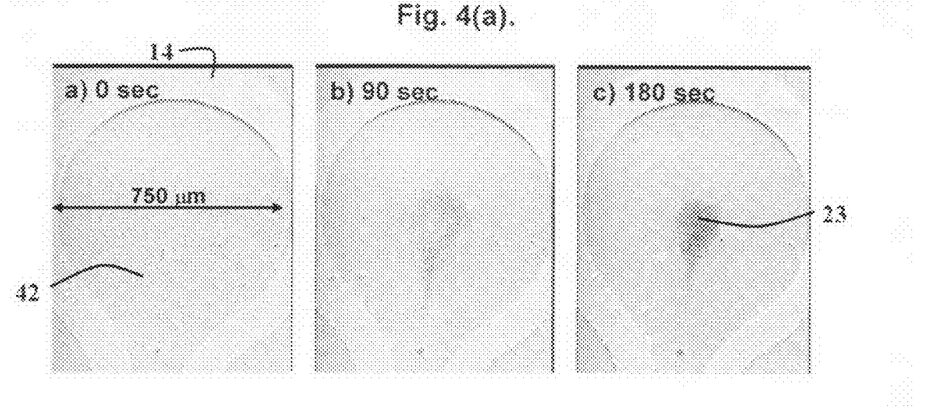

FIG. 4 a) shows the focusing of the spores 16 on a single circular surface 42 at various time intervals. As may be seen, in the absence of the potential difference the spores 16 are randomly distributed in the solution. After the application of the potential difference for 90 seconds, a large number of spores 16 are focused in the centre of the surface 42. After a further 90 seconds, the spores are tightly focused in a spot 23 in the centre of the surface 42.

The speed of focusing is dependent on the frequency of the applied potential difference and the conductivity of the liquid. Table 1 shows optimal frequencies for focusing the spores 16 from potassium chloride solutions of differing conductivities. A decrease in the speed of focusing is observed in solutions of high conductivity which may, however, be compensated by higher voltages.

TABLE 1

| Conductivity/mSm$^{-1}$ | Optimal frequency/Hz |
|---|---|
| 10 | 600 |
| 30 | 1000 |
| 70 | 2000 |
| 90 | 2500 |

EXAMPLE 2

The electrode configuration 37 of FIG. 3, in which the circular surfaces 42 of each electrode 38, 39 are 575 µm and the gap size is 100 µm, is used to focus spores 16 of *bacillus globiggi* (~800 nm) from a 30 mS/m potassium chloride solution containing ~10$^5$ spores/ml at an applied alternating potential difference of 1 kHz frequency at 10V.

The number of spores 16 observed at 15 second intervals in the centre of a circular surface is examined under a high magnification microscope at various time intervals.

Figure 4B:
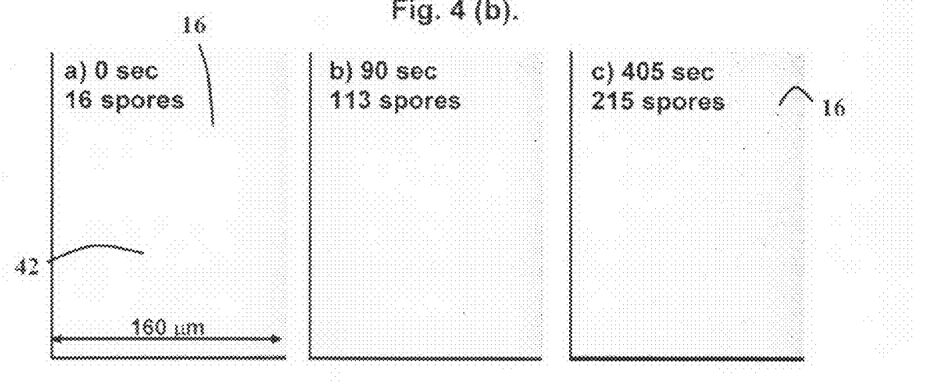
Figure 5A:
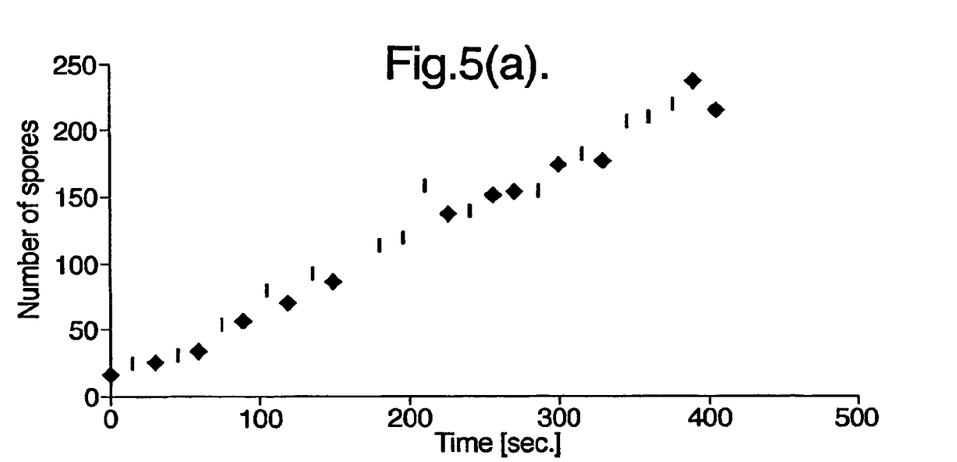

FIG. 4 b) shows that in the absence of the applied potential difference sixteen spores 16 are present. After the application of the potential difference for 180 seconds the number is 113 and rises to 215 after 405 seconds. FIG. 5 a) shows the rise in spore number plotted against time.

The electrode configuration of FIG. 3 clearly increases the local concentration of spores by collecting them on the electrode surface 42. It is expected that optimisation of parameters will lead to a more rapid focusing of spores from suspensions of this concentration.

As mentioned above, optimum focusing of particles is achieved when the size of the vortices are limited to just below the radius of the circular areas of the electrode so that there is no overlap of vortices originating at opposite points on the circumferential edge.

Figure 4C:
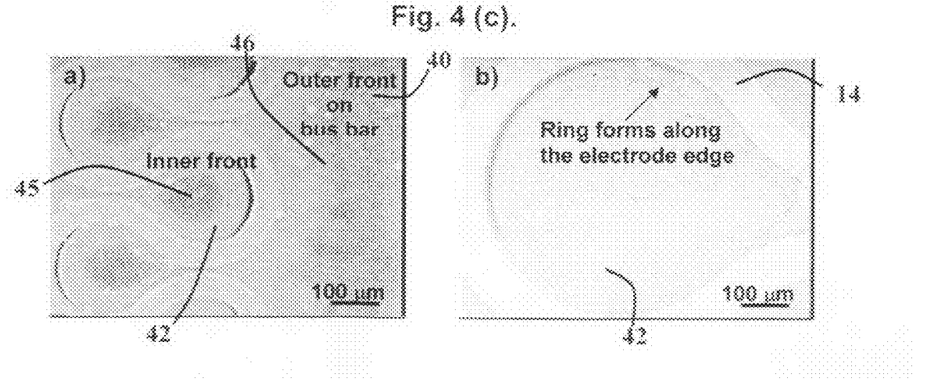

FIG. 4 c) shows the effect of the frequency of the applied potential difference on the size of the vortices formed in the liquid and thus the focusing of the particles on the circular surfaces 42. The collection fronts 45, 46 observed on the bus bar and on the surfaces 42 provides a control means allowing certainty that the diameter of the surfaces 42 are appropriate to the frequency of the applied potential difference. However, if the diameter is much larger than the vortices, particles 16 will collect on the surface in a ring around the edge. If the diameter is smaller than the vortices, the vortices will overlap exerting an increased drag on the particles 16 which will no longer be retained on the surface 42 (see also FIG. 8).

EXAMPLE 3

The electrode configuration 37 of FIG. 3, in which the circular surfaces 42 of each electrode 38, 39 are 230 µm and the gap size is 55 µm, is used to focus spores of *bacillus globigii* (~800 µm) from a 10 mS/m potassium chloride solution at an applied alternating potential difference of varying frequency at 10V.

Figure 5B:
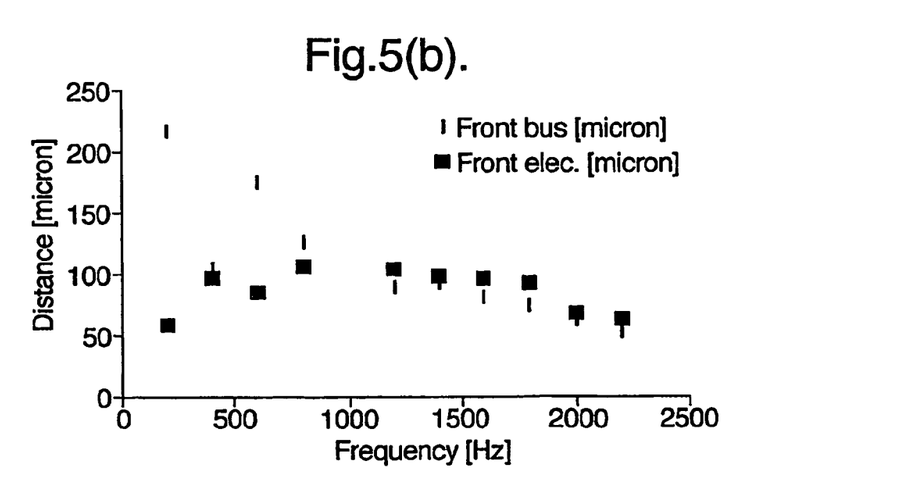

FIG. 5 b) shows a plot of the distance of the collection front from the edge of the circle as a function of frequency. As may be seen at the vortices are larger at lower frequencies.

EXAMPLE 4

The electrode configuration of FIG. 3, in which the circular surfaces 42 of each electrode 38, 39 are 575 µm and the gap size is 100 µm, is used to focus fluorescent latex beads of 110 nm diameter from a 1 mS/m potassium chloride solution at an applied alternating potential difference of 10V at 600 Hz frequency.

Figure 6:
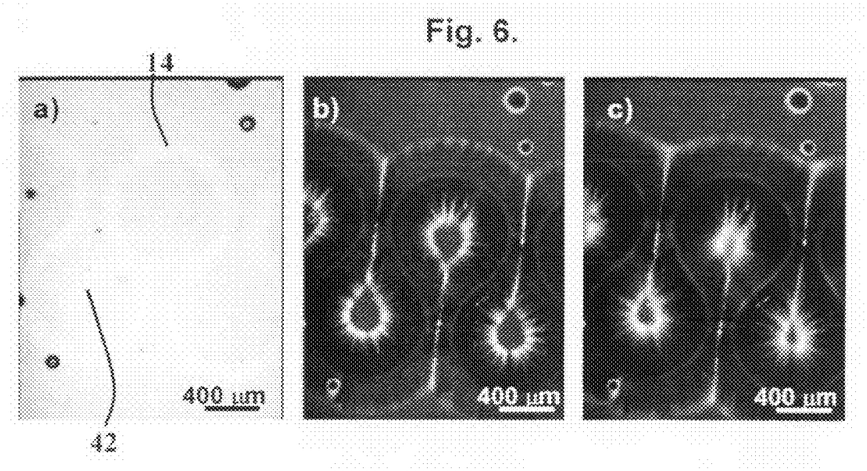
FIGS. 6 is a photograph showing the collection of virus sized, fluorescent latex beads on the electrode surfaces of the embodiment of FIG. 3.

Referring now to FIG. 6, in the absence of the applied potential difference a transmitted light photograph is not instructive. However, after 60 seconds and 120 seconds, fluorescence from the beads clearly shows them concentrated in the middle of the surfaces 42. The area at the top of the bus bar shows only background fluorescence of randomly distributed particles.

The concentration of virus size particles is an encouraging result in view of the fact that viruses may be smaller than other particles and therefore more likely to recirculated with the bulk flow. However, an antibody coating or layer capable of binding viruses would mitigate this effect.

EXAMPLE 5

Figure 7:
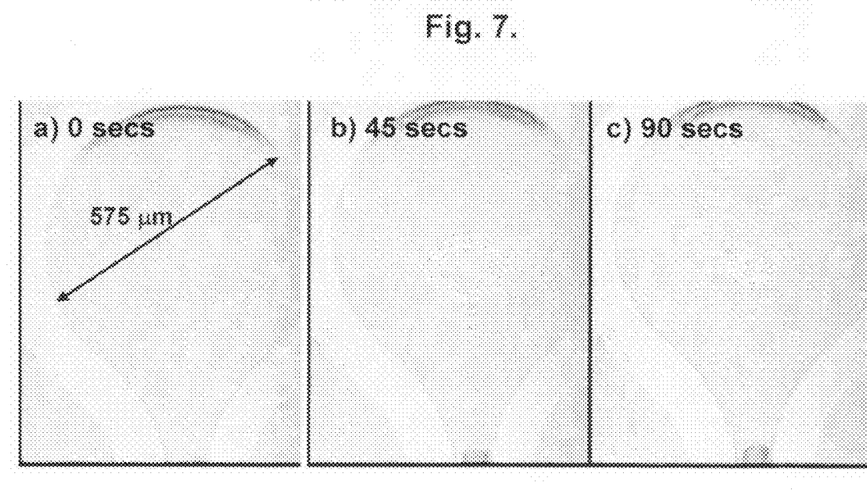
FIG. 7 shows focusing of yeast cells.

The electrode configuration 37 of FIG. 3, in which the circular surfaces 42 of each electrode 38, 39 are 575 µm and the gap size is 100 µm, is used to focus yeast cells (~5 µm) from a 0.1 mS/m potassium chloride solution at an applied alternating potential difference of frequency 600 Hz at 10V. Referring now to FIG. 7, after 45 seconds yeast cells 16 are drawn inwards onto the circular surfaces 42 in the form of a ring. After 90 seconds the cells are focused in a tight spot in the centre of the circular surfaces 42.

Figure 8:
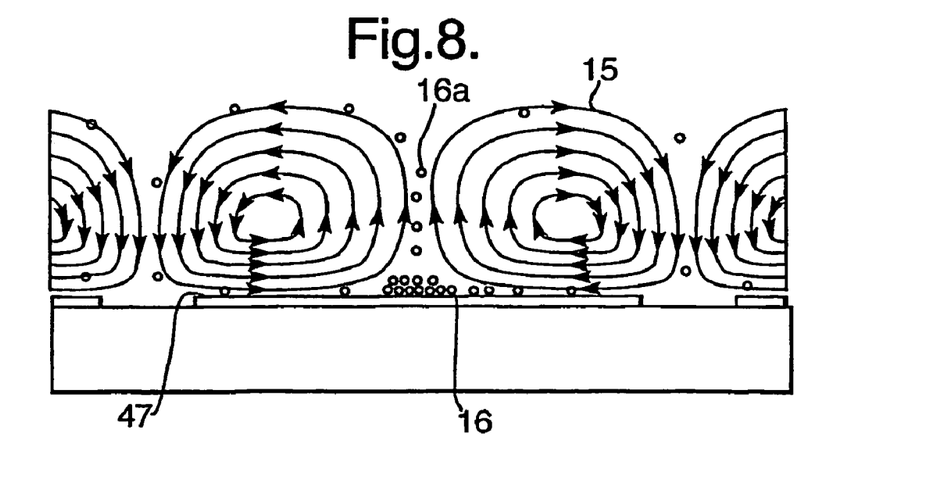
FIG. 8 is a schematic illustration highlighting the washing of particles from an electrode surface according to one aspect of the present invention.

Referring now to FIG. 8, the washing of particles over an electrode surface 47 on which particles are retained by an antibody or lectin coating or layer involves the selection parameters so that vortices 15 overlap above the electrode surface 47. As mentioned above, the overlap leads to increased drag on the particles 16, which returns unbound particles 16a to the bulk flow.

Figure 9A:
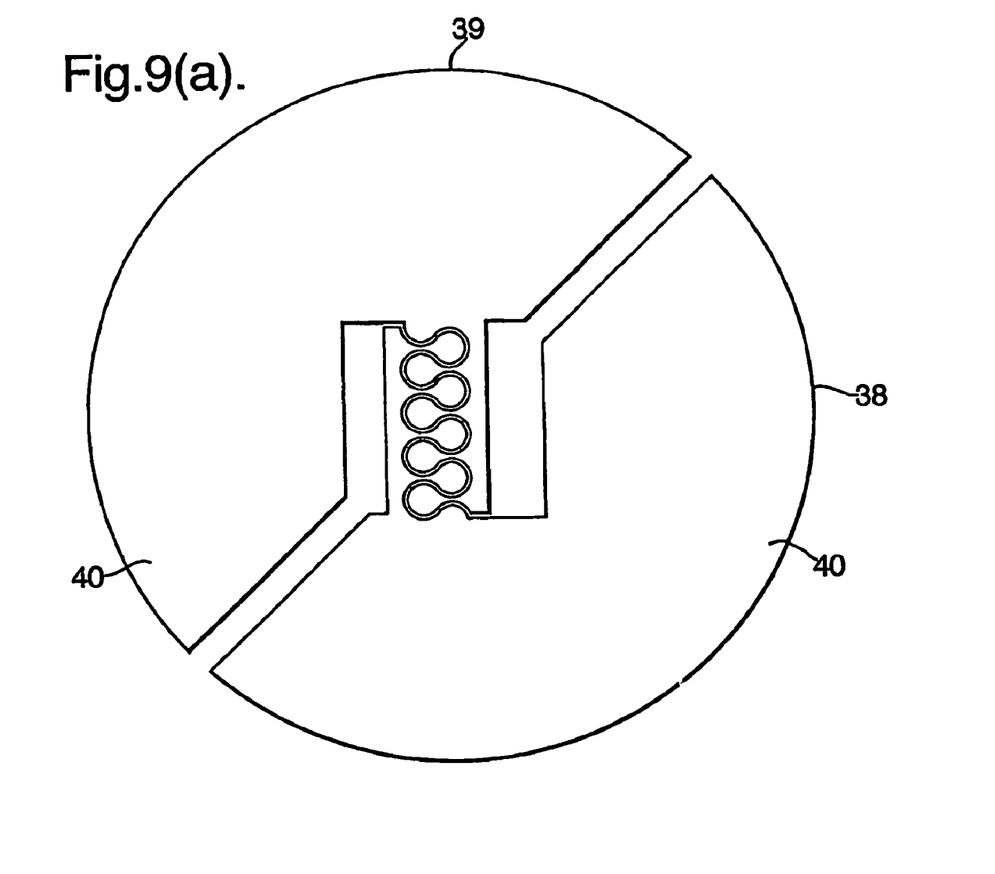
Figure 9B:
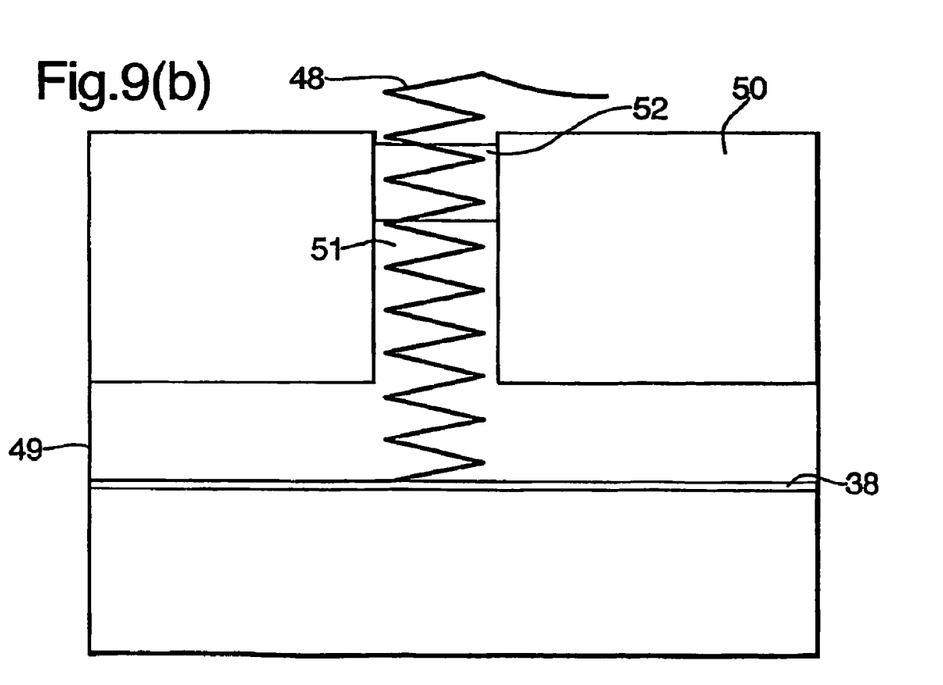

Referring now to FIGS. 9 a) and b), an electrode configuration similar to that described in FIG. 3 is provided in the centre of a circular SPR chip. The electrodes 38 39, which are gold, comprise semi-circular bus bars 40, which are connected to an alternating signal source (not shown) via a spring 48.

The arrangement may also be provided with semi-circular touch pads (not shown) so as to allow the slide to be rotated for different flow directions. The chip is fitted to a flow cell 49 provided with a lid 50 defining a central aperture 51 through which the spring 48, secured by a sealant glue 52, extends.

We claim:

1. Apparatus for collecting particles from a liquid, comprising a first electrode having an upper surface defining one or more substantially circular areas of a predetermined diameter separated from a counter electrode, having an upper surface bounding at least in part the circular area or areas of the first electrode, by a predetermined gap and means for applying an alternating potential difference of a predetermined magnitude at a predetermined frequency lower than the charge relaxation frequency of the liquid across the electrodes whereby particles from the liquid are focused onto the circular area or areas of the first electrode through an induced electro-osmotic flow in the liquid.

2. Apparatus according to claim 1, in which the upper surface of the counter electrode defines one or more substantially circular areas of predetermined diameter.

3. Apparatus according to claim 1, in which the electrode configuration is interdigital.

4. Apparatus according to claim 3, in which the upper surface of the first electrode defines a plurality of substantially circular areas sharing a first common horizontal axis.

5. Apparatus according to claim 4, in which the upper surface of the counter electrode defines a plurality of substantially circular areas sharing a second horizontal axis.

6. Apparatus according to claim 5, in which the first and second horizontal axis are parallel and the upper surface of the each electrode bounds at least a portion of the a circular area of the other electrode.

7. Apparatus according to claim 1, in which the predetermined diameter of the, or each circular area ranges from 200 to 1000 µm and the extent of the predetermined gap ranges from 10 to 200 µm.

8. Apparatus according to claim 1, in which the first and second electrodes comprise a metal capable of supporting surface plasmon resonance.

9. Apparatus according to claim 1, in which one or more circular areas on the first or each electrode are coated with an antibody or lectin layer.

10. Apparatus according to claim 1, in which the electrodes are disposed on glass, or an optically transparent, substrate.

11. Apparatus according to claim 10, in which the substrate is part of an SPR or MCLW sensor.

12. Apparatus according to claim 1, comprising an array of electrodes.

13. A method for collecting particles from a liquid, comprising the steps of i) introducing the liquid to a first electrode having an upper surface with one or more substantially circular areas of predetermined diameter separated from a counter electrode having an upper surface bounding at least in part the circular area or areas of the first electrode, by a predetermined gap and ii) applying an alternating potential difference of a predetermined magnitude at a predetermined frequency lower than the charge relaxation frequency of the liquid across the array whereby to induce an electro-osmotic flow in the liquid that focuses the particles from the liquid onto the circular area or areas of the first electrode.

14. A method according to claim 13, in which the frequency of the predetermined alternating potential induces an electro-osmotic flow extending from an edge of the first electrode substantially across the width of the radius of the or each circular area.

15. A method according to claim 13, in which the conductivity of the liquid ranges from 10 to 90 mS/m.

16. A method according to claim 13, in which the frequency of the applied potential difference ranges from 0.6 to 2.5 kHz at a voltage ranging from 1 to 50V.

* * * * *